US005525500A

United States Patent [19]

Khandke et al.

[11] Patent Number: 5,525,500
[45] Date of Patent: Jun. 11, 1996

[54] **CHROMATOGRAPHIC PROCESS FOR THE COPURIFICATION OF CHONDROITINASE I AND II PROTEINS FROM *PROTEUS VULGARIS***

[75] Inventors: Kiran M. Khandke, Nanuet; John Gotto, Suffern, both of N.Y.; Ursula Eul, Ramsey, N.J.

[73] Assignee: American Cyanamid Company, Wayne, N.J.

[21] Appl. No.: 231,534

[22] Filed: Apr. 22, 1994

[51] Int. Cl.$^6$ .............................. C12N 9/88; C07K 1/18; C07K 1/22
[52] U.S. Cl. .................. 435/232; 435/814; 435/815; 435/873; 530/415; 530/416
[58] Field of Search .................................. 435/232, 814, 435/815, 873; 530/416, 415

[56] References Cited

U.S. PATENT DOCUMENTS

| | | | |
|---|---|---|---|
| 4,696,816 | 9/1987 | Brown | 424/94 |
| 5,198,355 | 3/1993 | Kikuchi et al. | 435/232 |
| 5,292,509 | 3/1994 | Hageman | 424/94.61 |

FOREIGN PATENT DOCUMENTS

| | | |
|---|---|---|
| 0576294 | 12/1993 | European Pat. Off. . |
| 0613949 | 9/1994 | European Pat. Off. . |
| 2122588 | 6/1987 | Japan . |
| 698769 | 4/1994 | Japan . |
| 1067253 | 2/1966 | United Kingdom . |

OTHER PUBLICATIONS

Yamagata et al. (1968) *J. Biol. Chem.*, 243(7), 1523–1535.
Pharmacia (1974) *Affinity Chromatography, Principles and Methods,* Pharmacia Fine Chemicals, Uppsala, Sweden, pp. 56–57.
Kitamikado et al. (1975) *Appl. Microbiol.*, 29(3), 414–421.
Sato et al, (1986) *Agric. Biol. Chem.*, 50(4), 1057–1059.
Sato et al, (1994) *Appl. Microbiol. Biotechnol.*, 41(1), 39–46.

*Primary Examiner*—Michael G. Wityshyn
*Assistant Examiner*—Jon P. Weber
*Attorney, Agent, or Firm*—Darby & Darby

[57] ABSTRACT

A chromatographic process for the copurification of chondroitinase proteins useful in ocular surgery for non-surgical disruption of chondroitin sulfate, the molecule which mediates the attachment between the retina and vitreous body in the human eye. The process involves the use of ion exchange resins in conjunction with an affinity elution with chondroitin sulfate to afford copurification of the proteins.

18 Claims, 1 Drawing Sheet

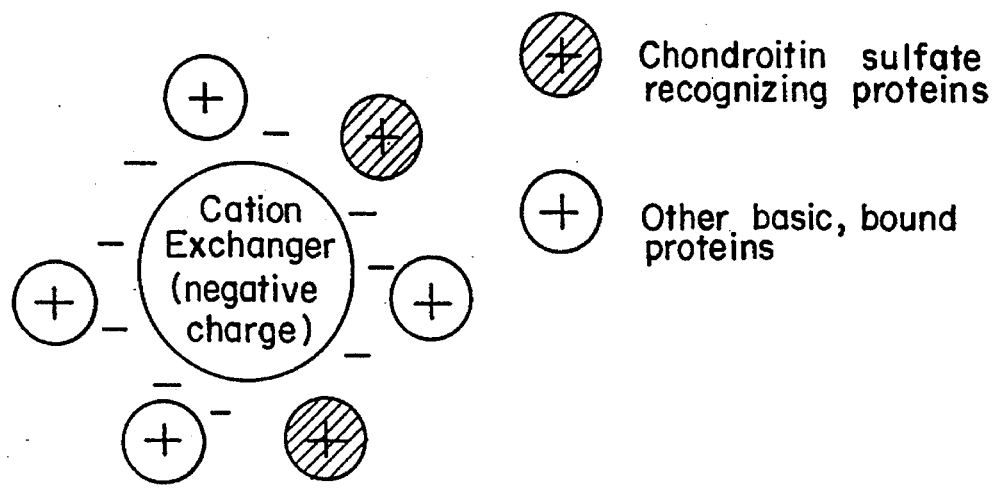
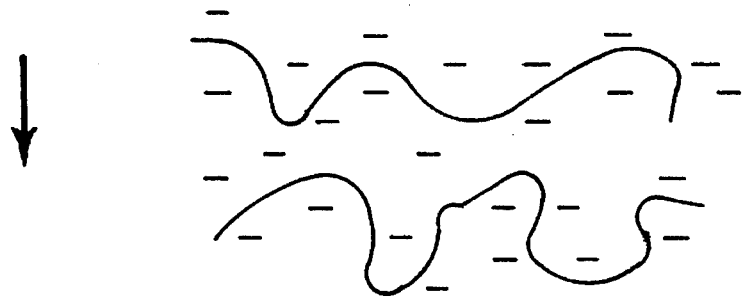
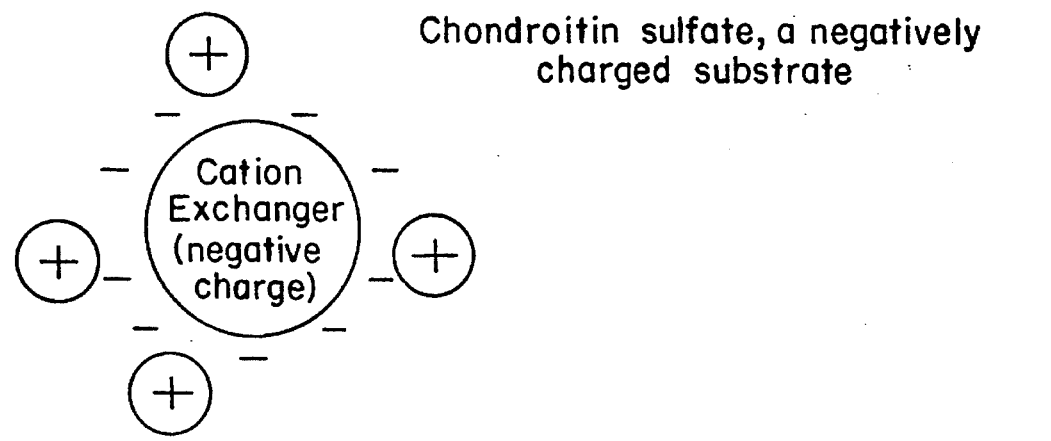
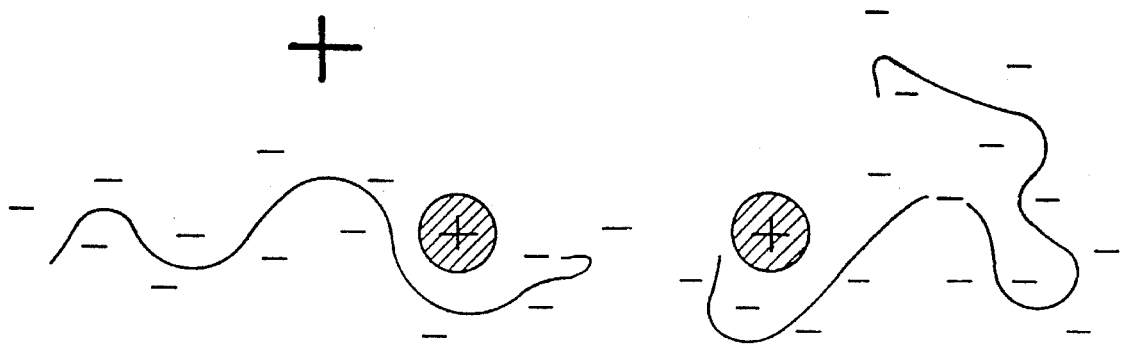

CHROMATOGRAPHIC PROCESS FOR THE COPURIFICATION OF CHONDROITINASE I AND II PROTEINS FROM *PROTEUS VULGARIS*

FIELD OF THE INVENTION

The present invention relates to a chromatographic process for the copurification of chondroitinase proteins. In particular, the present invention is directed to an affinity chromatographic process using ion exchange resins and optionally a metal chelating affinity support to copurify chondroitinase I and chondroitinase II proteins. Both these proteins recognize chondroitin sulfate and are eluted by it specifically.

BACKGROUND OF THE INVENTION

Macromolecules such as proteins, polysaccharides and nucleic acids exhibit only small differences in their physico-chemical properties within the individual groups, and their isolation to a high degree of purity, on the basis of these differences, for example by gel filtration or electrophoresis, is tedious, time consuming and difficult on large scale. In addition, decreases in the activity of the isolated products occur during the isolation procedures. One characteristic of biological macromolecules is their ability to bind other molecules specifically, reversibly and with high affinity. The complexes formed by these interactions of biological macromolecules and its substrate serves as a basis for purification. This technique is known as affinity chromatography.

Affinity chromatography is a separation technique which is based on the specific binding properties of biological molecules. Briefly, the methodology of affinity chromatography involves the attachment of a specific ligand to an insoluble support or matrix to form a conjugate which is then contacted with a "feed" containing the substance to be purified either in a column or batch configuration. Contact of the feed with the conjugate results in the substance that reacts specifically with the ligand becoming attached to the conjugate with all the remaining components of the feed passing through the column in the void volume. The absorbed substance is then eluted from the column by imposing conditions which dissociate it from the conjugated ligand. Preferably, the column can then be recycled and the affinity adsorbent reused for additional purifications.

Generally, in affinity chromatography, the ligand is covalently bound to the affinity support. However, severe shortcomings are encountered as a result of the instability of the covalent chemical linkages between the support and the ligand. Polysaccharide supports such as agarose using covalently coupled ligands which are susceptible to instability with respect to mechanical destruction and "ligand leakage" on prolonged washing. When the ligand is a polysaccharide (for example chondroitin sulfate) these same problems of microbial attack, mechanical destruction and "ligand leakage" become important considerations. When the affinity chromatography system uses an enzyme substrate as a ligand which is covalently bound to the support, the ligand is highly susceptible to breakdown by the enzyme during the purification process thus destroying the integrity of the ligand by destroying the ability of the ligand to bind to the enzyme. This would require replacement of the affinity chromatography system. Repeated cycling of most substrate based affinity systems invariably results in a lowering of binding capacity. This is true for covalently or non-covalently coupled systems, but the non-covalently coupled system can be brought back to functional use very cheaply.

An affinity chromatography system for the purification of biological materials comprising a charged polymer ligand non-covalently bound to a charged support is reported in copending application U.S. Ser. No. 08/031,158. In this affinity system the ligand and support are bound by ionic interactions which arise from oppositely charged materials. Utilization of the non-covalently bound ligand allows the non-functional ligand, after several cycles of use, to be easily washed off the support, followed by coupling fresh functional ligand on the same support thus saving the cost of the support, which is the major cost of the affinity chromatography system. The present invention involves the use of the non-covalent binding of ion exchange chromatography in combination with an affinity elution to copurify chondroitinase proteins.

Chondroitinases are enzymes that act on chondroitin sulfate, the molecule which mediates the attachment between the retina and the vitreous body of the human eye. The enzymes have potential use in ocular surgery as a means for rapid and specific non-surgical disruption of the attachment, facilitating removal of the vitreous body.

Chondroitinases are enzymes of bacterial origin which function by degrading polysaccharide side chains in protein-polysaccharide complexes, without degrading the protein core. Examples of chondroitinase enzymes are chondroitinase ABC, which is produced by *Proteus vulgaris* (*P. vulgaris*), and chondroitinase AC, which is produced by *A. aurescens*.

When the chondroitinase ABC enzyme is analyzed, it is found that it is actually composed of several components. The major component is a protein designated chondroitinase I. A second protein, designated chondroitinase II, has also been identified as a component of chondroitinase ABC enzyme.

Further, it has been discovered that for in vivo activity for the disinsertion of the vitreous body in ocular surgery, both protein components are necessary. By using a mixture of the two proteins, the desired enzymatic disinsertion is realized.

SDS-PAGE of the chondroitinase ABC enzyme produced by fermentation of *P. vulgaris* induced by the substrate, chondroitin sulfate, reveals a doublet band at approximately 110 kilodaltons. Separation and analysis of the doublet discloses that the lower band of the doublet represents the major component, chondroitinase I, while the upper band represents the second protein component, chondroitinase II.

The two chondroitinase proteins are produced by *P. vulgaris* in only small amounts and therefore an efficient method for copurification of the proteins is necessary.

There is thus a need for a method of co-purifying the chondroitinase proteins produced by *P. vulgaris*.

BRIEF DESCRIPTION OF THE DRAWINGS

FIG. 1 is a diagram illustrating the preparation and use of the affinity chromatography system of this present invention.

SUMMARY OF THE INVENTION

The present invention relates to an affinity chromatography system for the copurification of the chondroitinase I and chondroitinase II proteins that recognize chondroitin sulfate as a substrate.

In accordance with the present invention, the chondroitinase proteins are copurified from the crude extract of *P. vulgaris* fermentation mash by a stepwise process which involves:

(a) pH adjusting and diluting the extract;

(b) contacting the pH adjusted extract with a cation exchange resin to non-covalently bind the proteins;

(c) eluting the proteins with a solution of chondroitin sulfate;

(d) separating the chondroitin sulfate from the proteins by contact with an anion exchange resin; and (e) recovering the copurified chondroitinase proteins.

In another aspect of the invention, the proteins can be further purified by an additional step which involves the use of metal chelating affinity chromatograhy.

It is determined that the copurification process typically results in a weight/weight ration of approximately 60% chondroitinase I; 40% chondroitinase II, although ratios of up to approximately 80% chondroitinase I; 20% chondroitinase II are also obtained.

The chromatography system of the present invention involves the use of a high capacity strong cation exchange resin as shown in FIG. 1 to bind the chondroitinase proteins from the crude extract of the *P. vulgaris* fermentation mash. The majority of contaminating proteins are washed from the column and are not bound to the resin. The affinity elution of the chondroitinase proteins is accomplished with a solution of chondroitin sulfate. The coeluted proteins contain contamination of chondroitin sulfate and its digestion products. Final copurification occurs by loading the impure mixture on a high capacity anion exchange resin. The resin binds chondroitin sulfate and its digestion products, while the chondroitinase proteins flow through unbound. When done on a large scale, additional purification is accomplished using a resin which has been charged with nickel chloride and equilibrated. Most contaminating proteins flow through while the two proteins of interest bind. The chondroitinase proteins are then eluted from the resin. While nickel salts are preferred, other salts such as zinc, copper and iron are also acceptable.

A specific advantage of the present invention is that the proteins are coeluted from the *P. vulgaris* fermentation mash using a very simple chromatographic system. In addition the proteins are purified and retain their biological activity without a significant loss in yield or potency.

Another advantage is the ease at which the resins are prepared for use. Also, the resins can be recycled by a simple process of regeneration with an acid, alkali cycle. Other advantages include the reduced cost of the ion exchange resins.

The copurified proteins are suitable for use in complete disinsertion of the vitreous body in ocular surgery. If desired, the copurified proteins are readily separated from each other by additional process steps involving further cation-exchange chromatography. The individually purified proteins can be used in ratios other than those obtained by the copurification procedures.

DETAILED DESCRIPTION

Specifically, the copurification of the two proteins is performed as follows:

The *P. vulgaris* fermentation mash is centrifuged and the resulting pellet is suspended in a sodium phosphate buffer and then homogenized. The pH range of the suspension is preferable in the range of 5.8 to 7.4, most preferably 6.5 to 7.0. At a pH below 5.8, there is loss of activity due to precipitation of the proteins under the acidic conditions. The loss in activity is most significant at a pH below 5. Buffers other than phosphate can also be used. Preferably, the supernatant is adjusted to pH 6.8 using acetic acid and a conductivity of 3 milliSiemens/cm or lower. The appropriate conductivity is critical to achieve complete binding of the chondroitinase proteins to the subsequent cation exchange resin. It is determined in experiments that the conductivity must be below 3 milliSiemens/cm.

By doing these steps the efficiency at which the chondroitinase I and chondroitinase II proteins bind to the cation exchange resin which follows in the next step is increased. Smaller amounts are bound up to a conductivity of about 4–5 mS/cm. Higher conductivities result in the majority of the proteins being lost in the unbound fraction.

The pH adjusted, clarified and homogenized liquid is loaded onto a high efficiency cation exchange resin support, Macro-Prep™ High S (Bio-Rad Laboratories, Melville, N.Y. 11747) or other equally efficient resins. Among the charged support resin materials that are suitable for use in the present invention are other negatively charged groups for, example carboxymethyl(CM) can be also used. Several available supports, for example, other Macro-Prep™ acrylic supports; dextran, agarose, polyacrylamide, silica, polymethacrylate and other supports could also be used, as long as they carry negative charges and are capable of binding to the positively charged proteins. The chondroitinase I and II proteins bind to the resin while most of the protein contaminates flow-through. The resin is washed with pH 6.8 sodium phosphate buffer to near zero optical density and then equilibrated with pH 8.3 sodium borate solution.

This pH adjustment is important to obtain an effective/specific elution in the next step. This pH is close to the optimal pH for chondroitinase activity. At this pH there is a high degree of specific interaction between the chondroitinase proteins that are bound on the resin and the excess free substrate, causing the specific elution, while non-chondroitinase proteins (contaminants) remain bound. This pH is also close to the isoelectric point of the proteins, which allows for greater ease of elution. A pH of 8 to 9 can be used, although pH 8.3 to 8.5 gives the best results and is most particularly preferred. Other buffers in this pH range are also acceptable.

The affinity elution is accomplished with a 1% solution of chondroitin sulfate in water at a pH range of 7.0–9.5, preferably 8.5 to 9. The efficiency decreases if the elution pH is below 7. The pH is adjusted with sodium hydroxide. Other alkalies can also be used. The concentration of the substrate can be as low as 0.2% w/v and as high as 10% w/v. However, a lower percentage results in lower yields (below 0.5%) and a higher percentage results in higher levels of contaminating proteins due to increased conductivity of the eluent. The recovery of chondroitinase activity is about 72%, with a purity of 90 to 98% of the proteins being a mixture of the chondroitinase I and chondroitinase II proteins.

Although the pH of the chondroitin sulfate is adjusted; since there is no buffer in the solution (chondroitin sulfate is dissolved in deionized water), the pH is maintained close to the equilibrium pH of the resin (which is the borate buffer pH, used earlier before elution), in this case pH 8.3. The elution using the substrate results in higher purity compared to that obtained using salt solutions. In addition, salt eluted proteins require an additional desalting/diafiltration step before the next ion exchange step, which is not required for the affinity eluted proteins. This is because the conductivities needed for salt elution are about 20 fold more than 1% chondroitin sulfate solution.

The affinity eluted protein pool is simply adjusted to a pH of 6.8 with acetic acid and is loaded on a high efficiency anion exchange resin support Macro-Prep™ High Q (Bio-Rad Laboratories, Melville, N.Y.) (Q stands for quaternary ammonium) or other equally efficient resin. Other positively charged groups like DEAE can also be used.

Both the chondroitinase I and chondroitinase II proteins are co-eluted from the column in the unbound fraction and the chondroitin sulfate and its digestion products are bound to the resin. The resin is not only capable of removing chondroitin sulfate and increasing the purity of the product, but is also very effective in removal of endotoxin. The recovery in this step is 86% and the purity is increased to 95–99%.

On a 1000 liter scale, the purity of product after a sequential purification on a cation exchange column and an anion exchange column is less than that obtained under laboratory scale purifications. A third chromatography step using metal chelating affinity chromatography (MCAC) is used to improve purity of the proteins. The separation is based on differing abilities of proteins to interact with chelated metal attached to an insoluble support. Proteins bind mainly because of their content of histidine or cysteine. Varying the metal ions and the pH and salt concentration of the loading buffer establishes conditions under which the contaminating proteins will flow through and only the chondroitinase proteins bind to the charged resin. By using 50 mM imidazole in 50 mM tris-acetate at pH 8 in the presence of 0.2M NaCl as elution buffer, a purity of 98% is obtained without losing in vivo activity. The bound proteins are eluted with a solution of imidazole in starting buffer.

If desired, the copurified proteins are readily separated from each other by additional process steps. The individually purified proteins can be used in ratios other than those obtained by the copurification procedure. The eluate containing the copurified chondroitinase I and chondroitinase II proteins is adjusted to a pH of 6.8. The copurified proteins are subjected to cation-exchange chromatography on Macro-Prep™ High S column, pH 6.8. The column is washed with a borate buffer, pH 8.5. The two chondroitinase proteins are eluted from the column with a NaCl gradient of 0–150 mM in borate buffer. Alternatively, a single molarity solution of 50 mM NaCl in borate buffer is also equally effective. In each case, the chondroitinase I protein elutes in earlier fractions, separated from the chondroitinase II protein, which elutes in later fractions.

The following examples are provided by way of illustration and should not be interpreted as limiting the invention, many variations of which are possible without departing from the spirit or scope thereof.

EXAMPLE 1

A 10 L volume of *P. vulgaris* mash is centrifuged at 6,400 g for 20 minutes and the pellet resuspended in 10 mM sodium phosphate buffer at pH 6.8, then centrifuged again. The washed pellet is resuspended in the above buffer and homogenized through a Gaulin homogenizer at ~9000 p.s.i., three times. The homogenate (1.8 liters) is centrifuged at 17,700 g for 1 hour. Most of the supernatant (1.4 liters of 1.7 liters) is adjusted to a pH of 6.8 using 1M acetic acid and adjusted to a conductivity of 3 mS/cm by dilution with deionized water. Both of these steps ensure the efficient binding of the chondroitinase proteins to the cation exchanger that follows.

The adjusted, clarified, homogenate (2.4 liters containing 62.4K units of chondroitinase activity) is loaded on a Macro-Prep™ High S cation exchange column (Bio-Rad, Melville, N.Y.) of bed volume 340 ml, at a load of 184 units/ml resin. The chondroitinase proteins bind to the resin while the majority of contaminating proteins flow-through, unbound. The column is washed with ~4 bed volumes of 10 mM sodium phosphate buffer pH 6.8 to bring the optical density at 280 nm close to baseline. The resin is equilibrated with ~6 bed volumes of 40 mM sodium borate at pH 8.3.

The affinity elution is done using a 1% solution of chondroitin sulfate (Fluka Biochemicals) in water, adjusted to a pH of about 8.5 to 9 with NaOH. The two proteins are specifically eluted as a sharp peak, in about half the bed volume. The recovery of chondroitinase activity is 72%, at a purity of 96 to 98% of the proteins being a mixture of the chondroitinase I and the chondroitinase II proteins.

The affinity eluted protein pool is adjusted to pH 6.8 with acetic acid and is loaded on a Macro-Prep™ High Q anion exchange resin (Bio-Rad, Melville, N.Y.) of bed volume 85 ml, equilibrated at pH 6.8. Both the chondroitinase proteins elute unbound in the flow-through, while the chondroitin sulfate and its digestion products are bound to the High Q resin. The removal of chondroitin sulfate and its degradation products is confirmed by sulfate microanalysis of the load and the flow-through. By this step, 99.6% of the sulfate in the load is removed and the remaining 0.4% can be accounted for by partial oxidation of the sulfur within methionines and cystines in the proteins during ashing. In addition to the removal of chondroitin sulfate and its products, there is a increase in purity to about 98–99%. The recovery in this step is 38.3K units of chondroitinase, or 86%.

EXAMPLE 2

A 2.6 L volume of *P. vulgaris* mash is pelleted at 6,400 g for 20 minutes and the pellet resuspended in 350 ml of 10 mM sodium phosphate buffer pH 6.8 and centrifuged again. The pellet (142 g) is resuspended in 350 ml of deionized water and homogenized for three passes at about 10,000 p.s.i.. The homogenate is clarified by centrifugation at 17,700 g for 1 hour and the pH adjusted to 6.8 with 1M acetic acid and diluted to a conductivity of 3 mS/cm with deionized water. The adjusted clarified homogenate (16.2K units in 850 ml) is loaded onto a Macro-Prep™ High S column (Bio-Rad, Melville, N.Y.) of bed volume of 105 ml (154 units/ml resin). The column is then washed with about 2 bed volumes of 10 mM sodium phosphate buffer pH 6.8, followed by about 8 bed volumes of 40 mM sodium borate buffer of pH 8.3. The chondroitinase proteins are next co-eluted with 1% chondroitin sulfate in deionized water adjusted to pH~9 with 1M NaOH, at a purity of about 96–98% and a recovery of 88%. This eluted fraction is then adjusted to pH 6.8 with 0.1M acetic acid and loaded on a Macro-Prep™ High Q column (Bio-Rad, Melville, N.Y.) of bed volume 10.5 ml, equilibrated in 10 mM sodium phosphate buffer pH 6.8. The chondroitinase proteins are collected in the flow-through at a recovery of 95% and a purity of about 98 to 99%. The overall recovery from mash to purified proteins is 73%.

EXAMPLE 3

A 1000 L *P. vulgaris* fermentation is produced, with a final chondroitinase potency of 7.9 u/ml. The fermentation is diluted with 2000 L of deionized water and cooled to 12° C. The diluted mash is centrifuged at a flow rate to 80 L/minute to remove the fermentation broth. The wet mash solids are diluted with deionized water prior to homogenization. The 200 L of wet cells are homogenized in three passes using the Gaulin M3 Homogenizer at 8000 psi and a flow rate of 5 L/minute. The homogenate is diluted with deionized water prior to clarification to lower the conductivity further and then centrifuged to remove cell debris. The clarified homogenate is diluted further to lower the conductivity below 3 mS/cm.

This material (570 L) is loaded onto a 24L Macro-Prep™ High S column cation exchange (Bio-Rad, Melville, N.Y.) that has been equilibrated with 10 mM sodium phosphate pH 6.8. The flow rate is 1 L/minute. After loading, the resin is washed with about 3 bed volumes of 10 mM phosphate pH 6.8 and then equilibrated with 40 mM borate pH 8.3 (5 bed volumes) until the appropriate pH for elution is achieved. A 15% portion of the loaded activity does not bind to the resin and is detected in the flow through. Elution is carried out with 1% chondroitin sulfate at pH 8.9 and is monitored by absorbance at 280 run. After 9 L elutes and the absorbance begins to increase, fractions of 5 L are collected. Each fraction is analyzed by SDS-PAGE and activity assay. The desired fractions are combined, resulting in a recovery of 5.35 million units and a step yield of 82%. Purity by SDS-gel is 81%.

The pH of the High S eluate is adjusted to 6.9 using 1M acetic acid prior to loading onto a 3 L Macro-Prep™ High Q column(Bio-Rad, Melville, N.Y.). The feed is loaded onto the resin at 1780 u/ml resin at a superficial linear velocity of 100 cm/hr. The chondroitinase proteins are recovered in the flow-through, which is collected as one pool. Step yield from the anion exchange column is 96%. The flow through (9.95 L containing 5.14 million units) is concentrated by ultrafiltration, using a 30K spiral wound cartridge, to about 2 L before diafiltration against Water for Injection. The retentate is then lyophilized. Purity of the final lyophilized powder is 94% by area % stain from SDS-gels.

EXAMPLE 4

A chondroitinase preparation resulting from a 10 L fermentation is used. The mash is processed as described in Example 1. Side fractions containing the contaminating proteins are included to simulate the low purity obtained on large scale. This allows for a preparation after the High Q step that is similar to that obtained on the large scale (i.e., about 90%). This now becomes the starting preparation to standardize the third, metal affinity purification step. The purity of the eluate from the Macro Prep High Q by SDS-gel is approximately 90%.

For the final metal affinity purification step, a chelating Sepharose™ (Pharmacia LKB Biotechnology, Inc., Piscataway, N.J.) column with a bed volume of 23 ml is prepared. The resin is washed with deionized water, then charged with one bed volume of 0.1M nickel chloride. The resin is washed with water to remove unbound nickel and then equilibrated with the loading buffer (50 mM Tris-acetate pH 8.0, 0.2M NaCl). To the eluate from the High Q column, which contains low concentration of phosphate, 1M Tris-acetate, pH 8 and 2M NaCl are added to make a protein solution with the final concentration of the loading buffer. The prepared sample is loaded onto the column at 430 u/ml resin. The flow rate is 150 ml/hr corresponding to a superficial linear velocity of 75 cm/hr. After the sample is loaded, the resin is washed with loading buffer (approximately 5 bed volumes). Analysis of the flow through by activity assay and SDS-PAGE shows that most of the contaminating proteins, but less than 0.5% of the loaded activity, are recovered in this fraction. Elution with 50 mM imidazole in starting buffer results in the elution of a single protein peak, collected in fractions which are analyzed by SDS-PAGE. The desired fractions are combined resulting in a yield of 89% and an estimated purity of 96–98%.

EXAMPLE 5

The experiment is repeated under the same conditions as Example 4, but with an increased load (900 u/ml resin). Yield off the column is 75%, purity by SDS-PAGE 98%. The eluate is concentrated, diafiltered into water and lyophilized.

EXAMPLE 6

A 1000 L *P. vulgaris fermentation* with a potency of 7.5 u/ml mash is initially processed as described in Example 2. Purity of the eluate from the Macro-Prep™ High Q (Bio-Rad, Melville, N.Y.) column by SDS-PAGE is 83.9%. A column with a diameter of 18 cm is packed with approximately 9 L of Chelating Sepharose™ Fast Flow resin (Pharmacia LKB Biotechnology, Inc., Piscataway, N.J.). After the resin has been washed with water, it is charged with nickel chloride and equilibrated with pH 8 Tris-acetate buffer, 50 mM containing 0.2M sodium chloride. The High Q flow-through is adjusted to a final concentration of 50 mM Trisacetate pH 8 and 0.2M NaCl. The prepared feed is loaded onto the column at 600 u/ml resin and a flow rate of 19.2 L/hour corresponding to a superficial linear velocity of 75 cm/hour. The chondroitinase proteins are eluted from the column with an elution buffer, made of 50 mM imidazole in starting buffer. Step yield is 89% and the purity of the product is increased from 83.9% to 96.4%.

We claim:

1. A process for the copurification of the chondroitinase I and chondroitinase II proteins produced by *Proteus vulgaris*, said process comprising:

(a) preparing a clarified homogenate of *P. vulgaris*, the homogenate having a pH of 5.8 to 7.4 and a conductivity of 3 milliSiemens or lower;

(b) loading the homogenate onto a negatively charged cation exchange resin chromatographic support so that any positively charged proteins comprising chondroitinase I and chondroitinase II in the homogenate form a non-covalent bond with the negatively charged support;

(c) equilibrating the resin to a pH at which there is specific elution of chondroitinases I and II by chondroitin sulfate;

(d) affinity-eluting, in pools, the chondroitinase proteins from the support with an aqueous solution of chondroitin sulfate at pH 7.0–9.5;

(e) loading the affinity eluted protein pools from step (d) onto an anion exchange resin chromatographic support to yield an unbound eluate; and (f) recovering the chondroitinase I and chondroitinase II proteins in the unbound eluate from step (e).

2. A process as defined in claim 1, wherein in step (a) the clarified homogenate is prepared from substrate-induced *P. vulgaris*.

3. A process as claimed in claim 2, wherein said substrate is chondroitin sulfate.

4. A process as defined in claim 1, wherein said homogenate has a pH of 6.5–7.0.

5. A process as defined in claim 1, said cation exchange resin is equilibrated in step (c) to a pH of 8–9.

6. A process as defined in claim 1, wherein the pH of the chondroitin sulfate solution of step (d) is 8.5–9.0.

7. A process as defined in claim 1, wherein the concentration of the chondroitin sulfate solution of step (d) is 0.2%–10% w/v.

8. A process as defined in claim 1, which includes a further purification step which comprises contacting the eluate from step (f) with a metal chelating affinity chromatography support to further bind the chondroitinase proteins, eluting with an appropriate solvent, and recovering the copurified chondroitinase proteins.

9. A process as defined in claim 8, wherein the metal chelating affinity chromatography support contains zinc or nickel as the chelating metal.

10. A process for the individual purification of chondroitinase I and chondroitinase II proteins produced by *Proteus vulgaris*, said process comprising:
  (a) preparing a clarified homogenate of *P. vulgaris*, the homogenate having a pH of 5.8 g to 7.4 and a conductivity of 3 milliSiemens/cm or lower;
  (b) loading the homogenate onto a negatively charged cation exchange resin chromatographic support so that any positively charged proteins comprising chondroitinase I and chondroitinase II in the homogenate form a non-covalent bond with the negatively charged support;
  (c) equilibrating the resin to a pH at which there is specific elution of chondroitinases I and II by chondroitin sulfate;
  (d) affinity-eluting, in pools, the chondroitinase proteins from the support with an aqueous solution of chondroitin sulfate at pH 7.0–9.5;
  (e) loading the affinity eluted protein pools from step (d) onto an anion exchange resin chromatographic support to yield an unbound eluate;
  (f) recovering the chondroitinase I and chondroitinase II proteins in the unbound eluate from step (e);
  (g) loading the proteins recovered in step (f) onto a cation exchange resin chromatographic support; and
  (h) separately eluting the chondroitinase I protein and the chondroitinase II protein using a solution of sodium chloride as an eluent.

11. A process as defined in claim 10, wherein in step (a) the clarified homogenate is prepared from substrate-induced *P. vulgaris*.

12. A process as defined in claim 11, wherein said substrate is chondroitin sulfate.

13. A process as defined by claim 10 wherein said homogenate has a pH of 6.5–7.0.

14. A process as defined in claim 10, wherein said cation exchange resin is equilibrated in step (c) to a pH of 8–9.

15. A process as defined in claim 10, wherein the pH of the chondroitin sulfate solution of step (d) is 8.5–9.0.

16. A process as defined in claim 10, wherein the concentration of the chondroitin sulfate solution of step (d) is 0.2%–10% w/v.

17. A process as defined in claim 10, which includes a further purification step which comprises contacting the eluate from step (f) with a metal chelating affinity chromatography support to further bind the chondroitinase proteins, eluting with an appropriate solvent, and recovering the copurified chondroitinase proteins.

18. A process as defined in claim 17, wherein the metal chelating affinity chromatography support contains zinc or nickel as the chelating metal.

\* \* \* \* \*